United States Patent [19]

Wehrli

[11] 4,219,660

[45] Aug. 26, 1980

[54] CONJUGATED DIENE DERIVATIVES

[75] Inventor: Pius A. Wehrli, North Caldwell, N.J.

[73] Assignee: Hoffmann-La Roche Inc., Nutley, N.J.

[21] Appl. No.: 809,591

[22] Filed: Jun. 24, 1977

[51] Int. Cl.$^2$ .................. C07C 69/76; C07C 69/78; C07C 79/18

[52] U.S. Cl. .................. 560/20; 260/340.9 R; 260/404; 260/465 D; 260/561 R; 260/584 R; 260/954; 424/311; 544/162; 562/574; 560/22; 560/23; 560/30; 560/33; 560/46; 560/47; 560/49; 560/65; 560/74; 560/83; 560/88; 560/110; 560/156; 560/231; 560/250; 560/253; 560/262; 560/266; 568/687; 568/704; 568/11; 568/423; 568/946

[58] Field of Search .................. 560/110, 20, 22, 49, 560/74, 88, 46, 47, 65, 83, 23; 260/465 D

[56] References Cited

U.S. PATENT DOCUMENTS

| | | | |
|---|---|---|---|
| 2,463,831 | 3/1949 | Ullyot | 560/110 |
| 2,533,085 | 12/1950 | Blicke | 260/501.17 |
| 2,767,207 | 10/1956 | Reasenberg | 560/110 |
| 2,976,244 | 3/1961 | Bennett | 560/110 |
| 3,149,031 | 9/1964 | Stoffel et al. | 424/311 |

FOREIGN PATENT DOCUMENTS

| | | | |
|---|---|---|---|
| 17086 | 9/1915 | United Kingdom | 560/110 |
| 632561 | 11/1948 | United Kingdom | 560/110 |
| 977965 | 12/1964 | United Kingdom | 560/110 |

OTHER PUBLICATIONS

Govindachari et al., as cited in CA 53, 12268–12271, (1959).
Babaeva et al., Kratk. Tezisy-Vses. Soveshch. Probl. Mekh. Geteroliticheskikh. Reakts, 1974, pp. 139–141.
Blicke et al., J.A.C.S. 79, pp. 5508–5512 (1957).
French Patent Abstract, 1399781, (1964).

*Primary Examiner*—Jane S. Myers
*Attorney, Agent, or Firm*—Jon S. Saxe; Bernard S. Leon; William H. Epstein

[57] ABSTRACT

There are disclosed herein derivatives of bisfunctionalized compounds, wherein said compounds have been formed by the introduction of a nitro group and a hydroxyl group in the form of an ester into a conjugated diene molecule by treatment of said conjugated dienes with nitric acid in the presence of a carboxylic acid anhydride. The novel compounds produced by this process are useful as bactericides, fungicides and valuable organic synthesis intermediates.

6 Claims, No Drawings

CONJUGATED DIENE DERIVATIVES

CROSS REFERENCE TO RELATED APPLICATIONS

This application is related to U.S. Patent Application Ser. No. 667,796, filed Mar. 17, 1976, now U.S. Pat. No. 4,079,076 which is a continuation-in-part application of U.S. Patent Application Ser. No. 566,589, filed Apr. 9, 1975, now abandoned, entitled NOVEL ISOPRENE DERIVATIVES.

BACKGROUND OF THE INVENTION

Conjugated dienes, particularly isoprene, are basic building blocks of natural and synthetic rubber. As a matter of fact, the $C_5$ structure of isoprene is the basic unit of many natural products. Natural products whose structures are composed of isoprene units are referred to as isoprenoids. While isoprene itself has not been encountered in nature, the biogenetic path of terpene syntheses involves the incorporation of the $C_5$ repeating unit into a large variety of open and ring structures. The isoprene molecule is, therefore, of considerable importance in the synthesis of natural products.

Attempts to synthesize natural products from isoprene normally involve the functionalization of isoprene. Successful functionalization of isoprene have involved the addition of anhydrous NCl to isoprene yielding a mixture of prenyl chloride and isoprenyl chloride, the direct halogenation of isoprene yielding mixtures of dihalomethylbutenes, and reaction with tosyl chloride to give positional and cis/trans isomer mixtures of $C_5$ chlorosulfones. The utility of the halogenated isoprenes, however, is quite limited due to the difficulty of replacing the halogen substituents selectively with other functional groups. In view of the considerable interest in the synthesis of natural products and other materials employing the isoprenoid unit, there is a continuing effort in the area of isoprene functionalization.

It has been found that isoprene and other conjugated dienes can be regiospecifically difunctionalized according to processes disclosed and claimed in U.S. Patent Application Ser. Nos. 566,589 and 667,796 to Wehrli, the disclosures of which are incorporated herein by reference. The difunctionalized compounds, because of the presence of the nitro group, are readily amenable to the transformation of said nitro group to other functional groups, e.g., amino, carbonyl, cyano, oximes, etc. The presence of the alkoxy carbonyl (ester) moiety has also been found to provide another reactive site. A distinct advantage of the processes of the aforementioned applications is that the resultant products are substantially in the trans configuration, respecting the disposition of the nitro and ester groups, as opposed to cis and trans mixtures, which are generally obtained when isoprene is bis-halo substituted. Another important advantage is that the nitro group attaches itself practically exclusively at the one position of the conjugated diene carbon skelton thereby obviating the need to separate any positional isomeric species.

A surprising feature was that the regiospecific difunctionalization proceeds with negligible polymerization of the conjugated diene starting material. This was unexpected in view of the ready polymerizability of conjugated dienes in acidic solution and in the presence of radical initiators, such as nitrous oxides, which cannot be excluded whenever nitric acid is employed.

Although the foregoing discussion has been directed to isoprene, it is equally applicable to conjugated dienes in general.

SUMMARY OF THE INVENTION

The process of the instant invention is carried out by treating a conjugated diene of the formula:

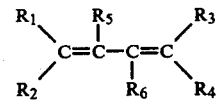

with nitric acid in the presence of an acid anhydride, preferably acetic anhydride, to form products of the formulae:

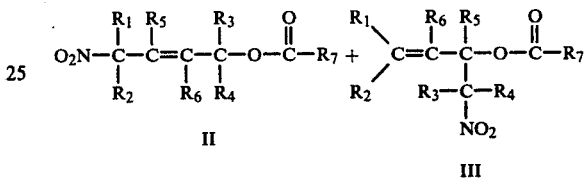

wherein $R_1$, $R_2$, $R_3$, $R_4$, $R_5$, $R_6$ are hydrogen or lower alkyl, and $R_7$ is lower alkyl.

The foregoing reaction is also applicable to cyclic conjugated dienes of the formula:

wherein n is a whole number integer from 1-10, to form compounds of the formula:

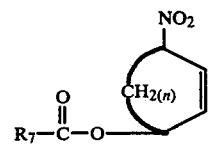

wherein $R_7$ and n are as above.

Compound III, in the presence of catalytic amounts of a mineral or lower or alkanoic acid or metal salts thereof, can be rearranged to form compound II. Typical mineral acids that may be employed are sulfuric, phosphoric, hydrochloric and the like. Typical lower alkanoic acids that may be employed are acetic, oxalic, malonic and the like. Typical metal salts that may be used are the copper, zinc, palladium platinum and the like. Particularly preferred is copper sulfate.

Compounds II, III and V may be subsequently transformed by hydrolysis to their respective alcohols by conventional procedures. The alcohols have the following formulas:

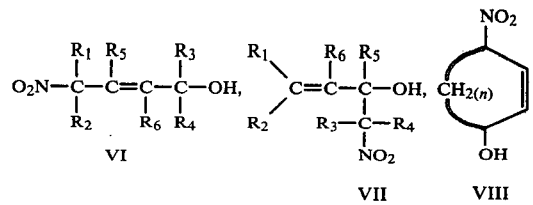

VI    VII    VIII wherein $R_1$, $R_2$, $R_3$, $R_4$, $R_5$, $R_6$ and n are as above.

Compounds II and III have been found to possess antimicrobial, bactericidal, and fungicidal properties. These compounds, as well as Compound V, are also useful as organic syntheses intermediates.

The isomeric species of each of the above compounds are separable by conventional techniques such as distillation and chromatography.

DESCRIPTION OF THE INVENTION

As used throughout the specification, the term "acid anhydride" refers to compounds having the formula:

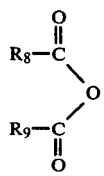

wherein $R_8$ and $R_9$, which may be the same or different, are alkyl.

The term "alkyl" refers to straight or branched chain hydrocarbon groups having from 1–20 carbon atoms, e.g., methyl, ethyl, propyl, butyl, octadecyl and the like. Especially preferred are lower alkyl groups wherein the above-mentioned chains contain from 1–6 carbon atoms. The term "lower alkanol" refers to straight or branched chain alcohols having from 1–6 carbon atoms. The term "alkylene" refers to straight or branched chain hydrocarbon groups having from 1–20 carbon atoms, e.g., methylene, propylene, butylene and the like. Especially preferred are lower alkylene groups wherein the above-mentioned chains contain from 1–6 carbon atoms. The term "alkoxy" refers to straight or branched chain alkoxy groups containing from 1–20 carbon atoms. Especially preferred are "lower alkoxy" groups containing from 1–6 carbon atoms. The term "acyl" refers to acyl groups having from 1–8 carbon atoms, e.g., acetyl, propionyl, butyryl and the like. The term "acyloxy" refers to acyloxy groups having from 1–20 carbon atoms. Especially preferred are lower acyloxy groups having from 1–6 carbon atoms such as acetoxy, propionyloxy and the like. The term "alkoxycarbonyl" refers to alkoxycarbonyl groups wherein the alkoxy moiety contains from 1–20 carbon atoms, preferably 1–6 carbon atoms. Typical alkoxycarbonyl groups are methoxycarbonyl, ethoxycarbonyl and the like. The term "aryl" refers to nuclear substituted or unsubstituted aryl groups. Typical aryl substitutents may be halogen, lower alkoxy, carboxy nitro, nitromethyl, amino and cyano. The terms halogen, unless otherwise stated, refers to bromine, chlorine, fluorine and iodine. The term alkali metal refers to lithium, sodium, potassium. The term alkaline earth metal refers to calcium, barium, and magnesium. The term lower alkanoic refers to mono or dicarboxylic acids having from 1–6 carbon atoms.

The difunctionalization is deemed to be regiospecific because the nitro group always adds at the 1-position of the isoprenoid moiety of compound I.

The regiospecifically difunctionalized conjugated dienes are formed by reacting said dienes with nitric acid in the presence of an acid anhydride, preferably acetic anhydride, in accordance with procedures described in detail in the aforementioned Wehrli applications.

Esters of compounds II and III are useful as bactericides and fungicides.

Alternatively, the crude nitro esters may be hydrolyzed and the respective alcohols, compounds VI and VII separated by conventional means. Compounds VI and VII have been found to possess bactericidal and fungicidal properties. In addition, compounds VI and VII may also be used as intermediates in the production of alcohol derivatives such as ethers, esters, urethanes, halides, etc.

The compounds of formulae VI, VII and VIII may be transformed into compounds of the formulae:

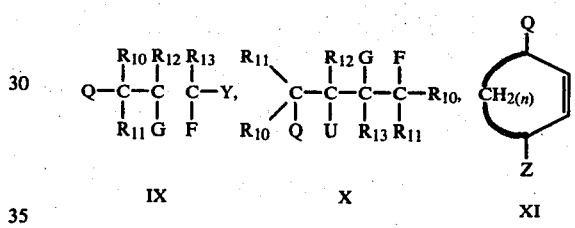

IX    X    XI wherein $R_{10}$, $R_{11}$, $R_{12}$, and $R_{13}$ are hydrogen or lower alkyl; Q is $-NO_2$ or $NHR_{14}$, where $R_{14}$ is hydrogen, lower alkyl, or acyl;

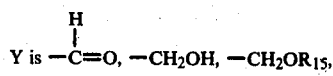

where $R_{15}$ is lower alkyl;

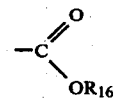

where $R_{16}$ is hydrogen or alkyl, aryl;

where X is halogen; $-CH_2-P^{\oplus}(Ar)_3 X^{\ominus}$ where P is phosphorus, Ar is aryl and X is halogen;

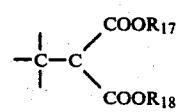

where $R_{17}$ and $R_{18}$ are lower alkyl;

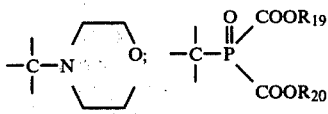

where $R_{19}$ and $R_{20}$ are lower alkyl;

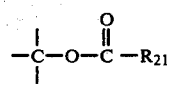

wherein $R_{21}$ is lower alkyl, aryl,

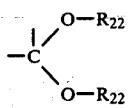

where $R_{22}$ and $R_{23}$ are lower alkylene;

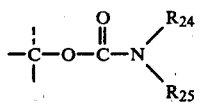

wherein $R_{24}$ and $R_{25}$ are hydrogen, lower alkyl and aryl; U is X; $-OR_{26}$, where $R_{26}$ is alkyl, aryl,

where $R_{27}$ is lower alkyl, aryl;

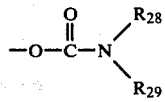

where $R_{28}$ and $R_{29}$ are hydrogen, lower alkyl, or aryl; $R_{10}'$, $R_{11}'$ are hydrogen or lower alkyl; Z may be any of U; carbonyl, and ketals derived from lower alkanols, optically active and optically inactive diols,

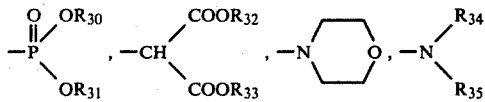

$SO_2R_{36}$, where $R_{30}$, $R_{31}$, $R_{32}$, $R_{33}$, $R_{34}$, $R_{35}$, $R_{36}$, are hydrogen, lower alkyl or aryl; and G and F are each hydrogen or may be taken together to form an additional bond.

The compounds of formulae IX, X, and XI are also useful as fungicides, bactericides and organic synthesis intermediates.

Compounds of formulae IX, where Y is a carbonyl group and G and F are an additional bond, may be formed by conventional processes for oxidizing a primary alcohol to an aldehyde. Typical oxidizing agents that may be employed are chromic acid, alkali metal salts thereof, potassium permanganate, silver oxide and the like. A preferred method of oxidation is one where Y in the above formulae is $-CH_2OH$ and said compound is treated with a mixture of sodium chromate, sulfuric acid and acetic acid.

Compounds of formulae IX, where Y is a carboxyl group and G and F are an additional bond, may be prepared by conventional processes for oxidizing a primary alcohol to an acid. Typical oxidizing agents that may be employed are the same as those used to oxidize an alcohol to an aldehyde. Also the Jones reagent may be used for this oxidation. A preferred process involves treating the above mentioned compounds where Y is $-CH_2OH$ with Jones reagent.

Compounds of the formulae IX, where Y is

and F and G are an additional bond, may be prepared by conventional processes for halogenating an alcohol. Typical halogenating agents that may be employed are thionyl chloride, phosphorous trihalides such as $PCl_3$ and $PBr_3$, phosphorous pentahalides such as $PBr_5$ and $PCl_5$, and the like.

Compounds of formula XI where Z is carbonyl, i.e. a ketone, may be prepared by conventional processes for oxidizing a secondary alcohol to a ketone. The oxidizing agents that may be employed are those used to prepare the aldehydes and acids of compound IX hereinabove.

Compounds of formulae X and XI where U and Z are halogen (where F and G are an additional bond) may be prepared by conventional procedures for halogenating an alcohol. The procedures used to prepare like compounds of formula IX may also be used for compounds of formulae X and XI.

The halogenated compounds of formulae IX, X (where F and G are an additional bond), and XI, particularly the brominated compounds, may be further reacted to form other useful compounds. Typical compounds that may be formed are the triarylphosphonium-halide derivatives, particularly the triphenylphosphonium bromide derivative. Such a compound is typically prepared by reacting a compound of formulae IX, X, or XI with a triarylphosphine in an inert solvent. Typical inert solvents that may be employed are pentane, hexane, octane, isooctane, benzene, toluene, diethyl ester, tetrahydrofuran, dioxane and the like.

The aforementioned halo derivatives of compounds IX, X (where F and G are an additional bond) and XI, may also be transformed into the corresponding 1,4 oxazines, lower alkyl diesters of dicarboxylic and phosphonic acids by treatment with morpholine, the lower alkyl dicarboxylic acid esters and the trilower alkyl esters of phosphonic acid, respectively. The foregoing derivatives may be prepared in the presence or absence of solvents. If prepared in the presence of solvents, the aforementioned inert solvents may be employed.

The compounds of formulae IX, X (where F and G are an additional bond) and XI where Q is nitro, may, selectively or completely, be reduced to form a saturated nitro compound or a saturated unsubstituted or acylated amino compound (the latter compound resulting from an acylation of the amino group which results from the reduction of the nitro group). The reduction may be accomplished by conventional chemical or catalytic means. A preferred means of accomplishing the aforementioned reduction is by employing a palladium on carbon catalyst in the presence of from about 50 to about 1000 psig of hydrogen. The reduction may be carried out in the presence or absence of solvent. If the reduction is carried out in a solvent, the solvents that may be employed are those mentioned hereinabove. The reduction may optionally be carried out in the presence of acids or bases. Preferred acids that may be employed, either singularly or in admixture, are lower alkanoic acids such as acetic acid and mineral acids such as HCl, HBr, $H_2SO_4$, $H_3PO_4$ and the like. For the partial reduction described above, the conventional Lindlar catalyst may be employed. Selective reduction involving only the nitro group may also be carried out in the presence of zinc dust employing solvents such as water or lower alkanols mixed with a mineral acid. Typical bases that may be employed are those mentioned hereinbelow.

The amino moiety of compounds IX, X, and XI resulting from the reduction of the nitro moiety may be simultaneously acylated if the reduction takes place in the presence of an anhydride of the type mentioned hereinbefore (in the presence of a compound such as pyridine) or a lower alkyl monocarboxylic acid.

An additional aspect of the foregoing reduction of the nitro group of compounds IX, X and XI is that there is provided a convenient way of preparing amino alcohols particularly 1,4-amino alcohols which are useful as intermediates in the preparation of polymers. In compounds of the formulae IX, X and XI where Y is $-CH_2OH$ the desired amino alcohol is obtained upon complete reduction of the aforementioned compounds as mentioned above. In the event that Y is

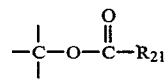

the corresponding alcohol may be obtained by hydrolysis of the aforementioned moiety. Said hydrolysis may be carried out in a conventional manner, typically in the presence of an aqueous base such as alkali and alkaline earth metal hydroxides, e.g. NaOH, KOH and the like and a lower alkanol.

Also contemplated within the scope of this invention is the preparation of fatty acid esters of either the nitro or amino compounds of formulae IX, X, and XI. These esters may be formed by employing conventional methods of esterifying alcohols, preferably by treating the alcohol with an acyl halide (preferably the acyl chloride) wherein the acyl moiety of said halide is the acyl moiety of the resulting ester.

A further aspect of this invention is a direct process for the preparation of 1,4-amino alcohols employing conjugated dienes as the starting material. The preparation of said alcohols is accomplished by nitroacyloxylating said conjugated diene as described in the aforementioned Wehrli applications, followed by rearrangement of the resulting mixtures of compounds II and III to form practically exclusively compound II. Compound II is then completely reduced to the saturated aminoacyloxy compound corresponding to formula IX. This compound is subsequently hydrolyzed with acid or base to the corresponding alcohol. The acids or bases that may be used are any of those mentioned hereinbefore. The various steps for the conversion of a conjugated diene to a 1,4-amino alcohol may be carried out as described hereinabove. A distinct advantage of this process is that it consists of only four steps and proceeds in a through fashion without the need for purification of intermediates.

The foregoing process represents a simple and direct method for 1,4-amino alcohols which have utility as intermediates for compounds having activity as central nervous system depressants (See U.S. Pat. No. 4,001,312—to Nakao et al) and polymeric compounds.

Another aspect of this invention is the formation of a compound of the formula:

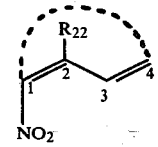

wherein $R_{22}$ is hydrogen or lower alkyl where the dotted line indicates that $C_1$ and $C_4$ may be taken together to form a ring.

Compound XII may be prepared from either a compound of formula II or a compound of formula IX where Q is nitro and Y is $-CH_2-X$, where X is as previously defined.

Compound XII is prepared from a compound of formula II by acid hydrolysis, followed by halogenation, with subsequent treatment with base. The acids that may be used are any of the mineral acids mentioned hereinbefore with $H_2SO_4$ being preferred. The bases used may be any of those mentioned hereinbefore. The halogenating agents used may be any of those mentioned hereinbefore with $PBr_3$ being particularly preferred.

The formation of compound XII proceeds by acid hydrolyzing a compound of the formula:

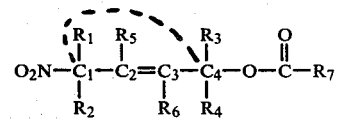

wherein $R_1$, $R_2$, $R_3$, $R_4$, $R_5$, and $R_6$ are hydrogen and $R_7$ is lower alkyl, and where the dotted line indicates that $C_1$ and $C_4$ may be taken together to form a ring, to form a compound of the formula:

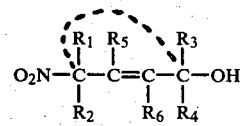

where $R_1$, $R_2$, $R_3$, $R_4$, $R_5$, $R_6$ and the dotted line as above followed by halogenation to form a compound of the formula:

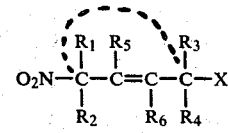

wherein $R_1$, $R_2$, $R_3$, $R_4$, $R_5$ and $R_6$ are as above and X is halogen followed by treatment with base to compound XII.

When compound XII is prepared from a compound of formula IX, as indicated above, the halogen is eliminated by conventional procedures. A preferred elimination procedure involves the use of an unsubstituted or lower alkyl substituted amine, preferably triethyl amine, to treat the halogenated compound of formula IX followed by treatment with a mineral acid, preferably hydrochloric acid.

Compound XII is useful as an intermediate for the ultimate preparation of terpenoid fragments which, in turn, are utile in the preparation of carotenoids. In particular, the reaction of compound XII with a lower alkyl senecioate results in the obtention of a $C_{10}$ terpenoid fragment of the formula

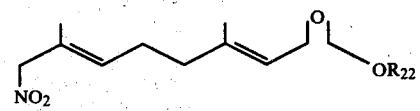

wherein $R_{22}$ is lower alkyl which can be potentially useful in Vitamin A acid and carotenoid manufacture. The reaction between a compound of formula XII and ethyl acetoacetate results in a $C_8$ fragment which can be further elaborated to carotenoids.

Compounds of formula IX where Y is $-CH_2OR_{15}$ may be prepared from compounds of formula XII by treating the latter with an alkali metal in the presence of a lower alkanol, said lower alkanol being the source of the alkoxy group $-OR_{15}$. In other words, if $-OR_{15}$ is to be methoxy then methanol is employed and so on.

$C_{10}$ dialdehydes, which in turn are valuable building blocks, for $C_{10}$ carotenoid fragments may be prepared by reacting dimers of isoprene with compounds of formula II to a double nitroacetoxylation product of the formula:

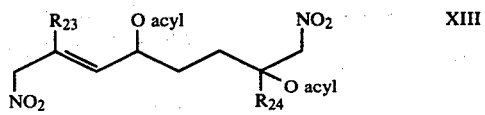

wherein $R_{23}$ and $R_{24}$ are lower alkyl and acyl is as defined hereinabove.

The above described procedures for the preparation of the nitro esters and derivatives thereof may be carried out batchwise or continuously, thus allowing for either small or large scale production.

The following non-limiting examples illustrate the instant invention. All temperatures are in degrees Centigrade and the ether used is diethyl ether.

EXAMPLE 1

Preparation of 4-Nitro-3-methyl-2-butenal

To a solution of 0.12 Mol sodium chromate, sulfuric acid and acetic acid in water, with cooling, a solution of 0.1 Mol 4-Nitro-3-methyl-2-butenol in benzene was added. After stirring 30 min. at 6° C., the layers were separated and the aqueous layer reextracted with benzene. Each benzene layer was washed with saturated NaCl solution. A red oil of approximately 80% weight yield was obtained.

An analytically pure sample was obtained via the sodium bisulfite adduct purification method. NMR spectroscopy showed an approximately 5:2 trans-cis isomer mixture.

EXAMPLE 2

Preparation of 4-Nitro-3-methyl-2-butenoic acid

A stirred solution of 0.1 Mol of 4-Nitro-3-methyl-2-butenol in acetone at 10°–15° was titrated with approximately 0.26 Mol of Jones reagent until the reaction mixture stayed dark orange colored. After 2 hours stirring at 10°–15° C. the mixture was decanted from the green chromium salts and the acetone removed. The residue was dissolved in ether and washed several times with saturated NaCl solution. After evaporation, the residue was crystallized from hot benzene and off-white crystals, mp 85°, were obtained. Two more recrystallizations from benzene yielded the pure nitroacid, mp 100°–102°.

EXAMPLE 3

Preparation of 3-chloro-3-methyl-4-nitro-1-butene and 4-chloro-2-methyl-1-nitro-2-butene To a solution of 0.1 Mol 4-nitro-3-methyl-2-butenol in methylenechloride at 15° C. was added dropwise 0.11 Mol of thionyl chloride. After evaporation of the methylene chloride the residue was distilled through a vigreux column collecting the tertiary chloride at 82°–92° C., 12 mm Hg and the primary chloride at 75° C., 0.4 mm Hg.

EXAMPLE 4

Preparation of 1-bromo-3-methyl-4-nitro-2-butene

To a solution of 0.1 Mol 4-nitro-3-methyl-2-butenol in benzene at 5° C. was added dropwise 0.036 Mol of phosphorous tribromide. The solvent was evaporated and the dark residue distilled through a vigreux column. Bp 100°/1 mm Hg.

A similarly prepared sample, b.p. 92°/0.5 mm Hg showed an approximate 4:1 isomer mixture by n.m.r. spectroscopy.

EXAMPLE 5

Preparation of 3-methyl-4-nitro-2-butenyl triphenylphosphoniumbromide

To a solution of 0.135 Mol of triphenylphosphine in benzene was added 0.1 Mol of 1-bromo-3-methyl-4-nitro-2-butene. The resulting phosphonium salt was recrystallized from methylene chloride-ethyl acetate and white crystals, m.p. 171°–172° C., were obtained.

EXAMPLE 6

Preparation of Tetrahydro-4-(3-methyl-4-nitro-2-butene-1-yl) (4H)-1,4-oxazine.

To a solution of 0.1 Mol of 1-bromo-3-methyl-4-nitro-2-butene in ether at 0° C. was added 0.2 Mol of morpholine and stirred at room temperature for two days. The residue, after filtration and evaporation of the solvent, was purified by column chromatography followed by Kugelrohrdistillation at 140°–150° oven temperature and oil pump vacuum. The product obtained was a yellow oil.

EXAMPLE 7

Preparation of 4-nitro-3-methyl-2-butene-1-phosphonic acid diethylester

To 0.1 Mol of 1-bromo-3-methyl-4-nitro-2-butene was added 0.1 Mol of triethylphosphite. The reaction was started by immersing the mixture into a 50° C. bath and completed under continued removal of bromoethane by distillation. The residue was purified via column chromatography over silica gel using ether as solvent. The product was obtained as a yellowish liquid.

EXAMPLE 8

Preparation of 2(-ethoxycarbonyl)-5-methyl-6-nitro-4-hexenoic acidethylester

To a suspension of 0.1 Mol of diethyl malonate and 0.25 Mol of sodium hydride in tetrahydrofuran was added a solution of 0.1 Mol 1-bromo-3-methyl-4-nitro-2-butene in tetrahydrofuran and stirred for 3 hours at room temperature. The reaction mixture was worked up via an acid extraction with ether. The excess of diethyl malonate was cautiously removed via distillation and the product purified by column chromatography over silica gel using ether/hexane 1:1 as eluent. A yellow oil was obtained.

EXAMPLE 9

Preparation of 4-nitro-1-butylacetate 6 g of crude 4-nitro-2-butene-1-acetate in 150 ml benzene was catalytically reduced with 1.2 g Pd/C and 50 lbs. of hydrogen. After evaporation of the benzene, the residue was distilled in a Kugelrohr apparatus. The product was obtained as a liquid.

EXAMPLE 10

Preparation of acetic acid 4-(acetylamino)-butylester 2-butene-1-ol-4-nitroacetate was reduced catalytically at 50° C. with Pd/C and hydrogen (1000 lbs. overnight in acetic acid. After evaporation, the residue was acetylated at room temperature overnight with acetic anhydride containing a few drops of pyridine. The reaction mixture was then distilled and a 95% pure fraction (colorless liquid) of the N,O-acyltated aminobutanol was collected at 137° C., 0.3 mm Hg.

EXAMPLE 11

Preparation of a mixture of N- and O-acetylated 1,4-aminobutanol

Reduction of 2-butene-1-ol-4-nitro acetate over Pd/C in acetic acid under 50 lbs. of hydrogen yielded, after evaporation of acetic acid, basification with ammonium hydroxide and extraction with methylene chloride, a mixture of N and O acetylated 1,4-aminobutanol. Silica gel chromatography yielded a sample of 1-amino-4-O-acetylbutane, which, on standing, changed to a mixture of N-, and O-acetylated 1,4-aminobutanol.

EXAMPLE 12

Preparation of 4-nitro-3-methyl-1-butanolacetate 41.6 g of crude acetic acid, (3-methyl-4-nitro-2-butene-1-yl) ester in 600 ml tetrahydrofuran containing 10% (v/v) acetic acid was catalytically reduced with 4.8 g Cu-mod. 5% Pd/CaCO$_3$ and 1000 lbs. of hydrogen at room temperature. After evaporation of the solvents, the residue was distilled, collecting a pure fraction of 13.5 g at 94° C., 0.1 mm Hg.

EXAMPLE 13

Preparation of 4-amino-3-methyl-1-butanol

Acetic acid (3-methyl-4-nitro-2-butene-1-yl) ester was catalytically reduced overnight at 95° C. over Pd/C-1000 lbs of H$_2$ in a water solution containing 10% (v/v) acetic acid and 4% (v/v) conc. hydrochloric acid. After filtration and evaporation, the residue was hydrolyzed at room temperature in a mixture of aqueous 1 N NaOH and ethanol. The reaction mixture was then brought to PH8 with 6 N HCl and the solvents were removed. Addition of alcohol and removal of inorganic material via filtration led to a dark solution. Evaporation of all solvent followed by Kugelrohr distillation yielded a slightly yellowish, viscous oil as the product.

EXAMPLE 14

Preparation of 4-amino-1-butanol 2-butene-1-ol-4-nitroacetate was reduced catalytically at 50° C. with Pd/C-H$_2$/1000 lbs. overnight in acetic acid. After evaporation, the residue was hydrolyzed in hot, diluted hydrochloric acid. The reaction mixture was then neutralized and extracted with n-butanol. The residue was flash distilled and a main fraction boiling at 105°–115° C. 12 mm Hg was collected.

EXAMPLE 15

Preparation of 4-nitro-1-butylpalmitate

To 0.1 Mol of 4-nitro-1-butanol in benzene was added 0.11 Mol of palmitoyl chloride and stirred at room temperature overnight. The benzene was evaporated and the residue taken up in a saturated sodium bicarbonate solution and extracted with methylene chloride. The product was crystallized from hot ethanol and white crystals, m.p. 35.5°–36.5° C., were obtained.

EXAMPLE 16

Preparation of hexadecanoic acid (4-amino-butyl) ester

Hexadecanoic acid (4-nitrobutyl)ester was reduced with zinc in EtOH/THF/6 nHCl for 30 minutes at 35°–35°. Work up in the cold via basification with ammonia and extraction with methylene chloride yielded a crude residue. Crystallization from ether furnished off-white crystals, m.p. 59°–61°.

EXAMPLE 17

Preparation of 4-nitro-3-methyl-1-butanol 2 g of 4-nitro-3-methyl-1-butylester was left at room temperature in 20 ml of a 15% (g/v) sulfuric acid solution in methanol overnight. After adding a solution of saturated sodium chloride, the compound was extracted with methylene chloride. The residue was distilled in a Kugelrohr apparatus (oven temperature 125°, oil pump vacuum). The product was obtained as a liquid material.

EXAMPLE 18

Preparation of 4-nitro-1-butanol 2.3 g of 4-nitro-1-butanol acetate was left at room temperature in 50 ml of a 15% (g/v) sulfuric acid solution in methanol overnight. After adding a solution of saturated sodium chloride, the compound was extracted with methylene chloride. The residue was distilled in a Kugelrohr apparatus. The material was obtained as a liquid.

EXAMPLE 19

Preparation of 1-acetoxy-4-nitro-2-cycloheptene

To 0.6 Mol of acetic anhydride were added at 25° C. 0.16 Mol 90% HNO$_3$ over 30 minutes. The mixture was stirred for an additional 15 minutes before 0.1 Mol of 1,3-cyclo-heptadiene was added over a 45 minute period, maintaining the temperature at 25° C. The reaction mixture was stirred for an additional 45 minutes before it was poured onto ice water and extracted with methylene chloride. An oily residue (100.5% weight yield) was obtained, which was purified by column chromatography, using silica gel and benzene/ethylacetate 4:1 as eluent. The product has the appearance of a yellow oil.

EXAMPLE 20

Preparation of 1-acetoxy-4-nitro-2-cyclopentene

To 0.6 Mol of acetic anhydride were added at 25° C. 0.163 Mol 90% HNO$_3$ over 45 minutes. The mixture was stirred for an additional 20 minutes before 0.1 Mol cyclopentadiene was added over a 1 hour period, maintaining the temperature at 25° C. The reaction mixture was stirred for an additional hour before it was poured onto ice water and extracted with methylene chloride. An oily residue (120% weight yield) was obtained. An aliquot was purified via Kugelrohr distillation removing first acetic acid/acetic anhydride followed by the product.

EXAMPLE 21

Preparation of 4-amino-2-cyclopentenol acetate 5 g of 1-nitro-3-O-acetyl-4-cyclopentene was reduced with zinc powder in ethanolic solution via the addition of 50 ml of conc. HCl at max 35° C. (ice cooling). after 5 minutes the reaction was quenched on ice and ammonia. Extraction with methylene chloride and evaporation yielded 3.1 g of crude product as a yellow viscous oil. Further purification was achieved via column chromatography over silica gel, using ethylacetate as eluent. The product, judged by n.m.r., is an approximate 1:1 cis/transisomer mixture.

EXAMPLE 22

Preparation of (Z,E)-N-[(3-acetyloxy)cyclopentane]-acetamide 20 g of 1-nitro-3-O-acetyl-4-cyclopentene was hydrogenated in acetic acid at 1000 lb H$_2$/50° overnight. Filtration and evaporation yielded a crude residue of 16.7 g to which was added 119 g of acetic anhydride and 2 drops of pyridine. An initial exotherm (approx. 70°-80°) was observed. After standing for 4 hours at room temperature, excess acetic anhydride and acetic acid were removed in vacuo and the residue, 36.3 g, distilled using a vigreux column. A main fraction, boiling at 153°/0.5 mm was collected.

EXAMPLE 23

Preparation of (Z/E)-3-aminocyclopentanol 10 g of 1-nitro-3-O-acetyl-4-cyclopentene was hydrogenated in acetic acid over 1 g of 10% Pd/C at 1000 lb H$_2$50° overnight. After filtration and evaporation a crude oily residue of 18 g was obtained. This residue was hydrolyzed in 75 ml 3n NaOH at 85°-100° for one hour. Cooling, followed by extraction with n-butanol yielded 7.4 g of crude 1,3-aminobutanol. The product was further purified via column chromatography over silica gel. The mass spectrum of the viscous material showed the molecular ion at m/e 101 and the ir spectrum showed strong absorptions in the NH and OH region at 3200-3400 cm$^{-1}$.

EXAMPLE 24

Preparation of 1,4-aminobutanol 420 ml acetic anhydride, was placed in a one liter 3 necked flask. Under stirring and cooling in an ice bath, 70 g of 90% nitric acid was added over a period of 40 minutes, while maintaining the inside temperature at 23°-25°. 32.3 g 1,3 butadiene; were introduced as a gas from a lecture bottle over a period of 2 hours, at 22°-25°. After the addition of butadiene was completed, the reaction was stirred for an additional hour at the same temperature. Work up was carried out by pouring the reaction mixture onto 400 ml of ice and water and extracting with 400 ml and 2×200 ml of methylenechloride. The organic layers were washed with 200 ml of ice water, dried over MgSO$_4$ and evaporated. The excess acetic anhydride is recovered for reuse. A crude residue of 86.9 g, a mixture of I and II, was obtained. The above residue, 86.9 g, was dissolved in 200 ml of methylenechloride and 2 g of Pd(PhCN)$_2$Cl$_2$ was added. After refluxing overnight, the mixture was filtered over a bed of celite and the solvent evaporated. A "rearranged" residue of 92.6 g was obtained. The above residue, 92.6 g, was dissolved in 900 ml of acetic acid, and hydrogenated at 1000 psi over 9 g of Pd/C 10% at 50° overnight. Filtration from the catalyst and evaporation yielded an oily residue of 141.6 g. To the above residue, 141.6 g, was added 300 ml of 2NHCl and 73.6 g of conc. HCl. After 30 minutes reflux, the reaction mixture was cooled in an ice bath, ca. 100 g of NaOH-pellets added cautiously and the product extracted with three 500 ml portion of n-butanol. Removal of the solvent left a dark residue with some inorganic material. This was removed by dissolving in methylenechloride, filtration and evaporation. A crude residue of 44.6 g was obtained which was purified by distillation. A colorless main fraction of 1,4-aminobutanol, 21.1 g (40%) bp 105°-116°/12 mm, was obtained.

EXAMPLE 25

Preparation of 1-Nitro-2-methyl-1,3 butadiene (from 1-Bromo-3-methyl-4-nitro-2-butene). To a solution of 0.1 Mol of 1-Bromo-3-methyl-4-nitro-2-butene in ether at 0° was added 0.12 Mol of triethylamine. The off-white crystals of triethylamine hydrobromide were filtered and the ether solution was washed with diluted hydrochloric acid. A light yellow oil in 88% yield was obtained.

A similarly prepared sample showed an approximate 2:7 trans/cis isomer ratio, as measured by n.m.r.

EXAMPLE 26

Preparation of 1-Nitro-2-methyl-1,3-butadiene (From acetic acid (3-methyl-4-nitro-2-butene-1-yl) ester). The nitroacetate was dissolved in a 10% sodium hydroxide solution and extracted several times with large quantities of hexane. A light yellow oil in 39% yield was obtained, showing identical n.m.r. absorptions as in the alternate of Example 25.

EXAMPLE 27

Preparation of 3,7-dimethyl-8-nitro-2,6-octadienoic acid methyl ester

To the lithium salt of methylsenecioate in THF at −70° was added an equimolar amount of 1-nitro-2-methyl-1,3-butadiene. Quenching in ice, followed by ether extraction yielded a crude product which was purified by Kugelrohr distillation and chromatography. The product had the appearance of a yellowish colored liquid.

EXAMPLE 28

Preparation of 2-acetyl-5-methyl-6-nitro-4-hexenoic-acid ethylester

To a solution of 0.1 Mol sodium ethylate in ethanol and 0.1 Mol of ethyl-acetoacetate was added 0.1 Mol of 1-nitro-2-methyl-1,3-butadiene. The reaction mixture, after 2 hours stirring at room temperature, was poured onto dilute HCl in ice, saturated with NaCl and extracted with ether. Evaporation of the solvent and excess of ethylacetoacetate yielded a crude oily residue which was purified by chromatography over silica gel using a hexane/ether, 2:3, mixture. The product was obtained as a yellow liquid.

EXAMPLE 29

Preparation of 4-nitro-1-methoxy-3-methyl-2-butene 0.1 Mol of 1-nitro-2-methyl-1,3-butadiene was added to a solution of 0.1 Mol of sodium in methanol and stirred overnight. The reaction mixture was quenched in ice and extracted with methylene chloride. The oily residue was purified via column chromatography. The product was obtained as a yellow liquid.

EXAMPLE 30

Preparation of 4-methyl-1-(2-methyl-3-nitro-1-propenyl)-4-(nitro methyl)-1,4-butanediol diacetate Into a solution of acetyl nitrate, prepared via the slow addition of 2.4 g of 90% NHO$_3$ to 17.5 g of acetic anhydride and stirring for ½ hour, was added slowly 1.5 g of 2,7-dimethyl-1,3,7-octatriene and under cooling. After stirring for a further 90 minutes, the reaction was quenched in ice and extracted with methylene chloride. A yellow oil of 3.6 g was obtained.

EXAMPLE 31

Preparation of 3-methyl-4-nitro-2-butene-1-ol-4-nitrobenzoate

To 0.1 Mol of 4-nitro-3-methyl-2-butenol in benzene was added 0.1 Mol of p-Nitrobenzoylchloride and stirred overnight. The benzene was evaporated and the residue was stirred in sat. sodiumbicarbonate solution for 1 hour. The solid was filtered and recrystallized from hexane. An off white crystalline product, mp 63°–66° C., was obtained.

EXAMPLE 32

Preparation of 3-nitro-1,2-benzenedicarboxylic acid, 2(3-methyl-4-nitro-2-butenyl)ester 0.1 Mol of 4-nitro-3-methyl-2-butenol and 0.1 Mol of 3-nitro-phthalic anhydride in toluene were refluxed for one hour. The toluene was evaporated and the residue was stirred in sat. sodiumbicarbonate solution. Acidification and extraction with ether, followed by column chromatography over silica gel and crystallization from toluene yielded an off white crystalline product, m.p. 130°–133°.

EXAMPLE 33

Preparation of 3-methyl-4-nitro-2-butene-1-ol-4-chlorophenylcarbamate

To 0.1 Mol of 4-nitro-3-methyl-2-butenol was added 0.1 Mol of melted p-chlorophenylisocyanate. The reaction mixture was allowed to stand at room temperature for several hours, before it was dissolved in hot benzene. After crystallizing overnight a solid by-product was filtered off and the benzene was evaporated. The residue was purified by dissolving in a hot hexane-benzene mixture, decanting, while hot, from an insoluble oil, followed by crystallization in a ice bath. The product was obtained as orange crystals, m.p. 79°–81°.

EXAMPLE 34

Preparation of 3-methyl-4-nitro-2-butene-1-ol-3,5-dinitrobenzoate

To 0.1 Mol of 4-nitro-3-methyl-2-butenol in benzene was added 0.1 Mol of 3,5-dinitrobenzoylchloride and stirred overnight. The benzene was evaporated and the residue was stirred in sat. sodiumbicarbonate solution for 1 hour. The solid product was filtered and recrystallized first from alcohol water and then from ethylacetate/hexane. The product was obtained as a yellow crystalline material, m.p. 111°–113°.

EXAMPLE 35

Preparation of 3-methyl-4-nitro-2-butene-1-ol-phenylcarbamate 0.1 Mol of 4-nitro-3-methyl-2-butenol and 0.1 Mol of phenylisocyanate were treated at 60°–80° C. for 3 hours. The reaction mixture was left for several hours at room temperature before dissolving it in hot benzene. The benzene solution was filtered and evaporated. The residue was crystallized from hot ligroin. Yellow crystals, m.p. 63°–66°, were obtained.

EXAMPLE 36

Preparation of 3-methyl-4-nitro-2-buten-1-ol-hexadecanoate

To 0.1 Mol of 4-nitro-3-methyl-2-butenol in benzene was added 0.1 Mol of palmitoylchloride and stirred overnight. The benzene was evaporated and the residue was taken up in sat. sodiumbicarbonate solution and extracted with ether. The product was crystallized from a 95% ethanol-water solution. Off white crystals, m.p. 30.5°–31.5° C., were obtained.

EXAMPLE 37

Preparation of 3-methyl-4-nitro-2-butene-1-ol-benzoate

To 0.1 Mol of 4-nitro-3-methyl-2-butenol in benzene was added 0.09 Mol benzoylchloride and stirred overnight. The benzene was evaporated and the residue was stirred with sat. sodiumbicarbonate solution and extracted with ether. The oily product was purified by column chromatography, yielding the product as a slight yellow liquid.

EXAMPLE 38

Preparation of 2,4-dichlorobenzoic acid (4-nitro-3-methyl-2-butenyl)ester

To 0.1 Mol of 4-nitro-3-methyl-2-butenol in benzene was added 0.1 Mol of 2,4-dichlorobenzoylchloride and stirred overnight. The benzene was removed, the residue taken up in sat. sodiumbicarbonate solution and in micrograms/ml (MCG/Ml) are tabulated in Table I.

TABLE I

| | Bacillus subtilis | Staph. aureus | E. Coli | Pseudo. aerug | Sacchar. cerev. | Paecilo. varioti |
|---|---|---|---|---|---|---|
| | + | + | − | − | fungi | mold |
| (structure 1) | 63 | 125 | 63 | 16 | <8 | 31 |
| (structure 2) | 125 | 125 | 63 | 63 | <8 | 125 |
| (structure 3) | 125 | 125 | 63 | 31 | <8 | 125 |
| (structure 4) | 31 | 63 | 63 | 63 | <8 | 125 |
| (structure 5) | 63 | 125 | 125 | 63 | 16 | 125 |
| (structure 6) | 250 | 2500 | 500 | 63 | 250 | 63 | extracted with ether. The crude product was purified by column chromatography over silica gel using methylenechloride as eluting solvent. A yellowish oil was obtained.

EXAMPLE 39

Preparation of 2-(3-Nitro-2-methyl-1-propenyl)-1,3-dioxolane 0.1 Mol of 4-nitro-3-methyl-2-butenal and 0.1 Mol of ethyleneglycol is benzene were refluxed for 1 hour, collecting 0.1 Mol of water in a Dean Stark trap. After cooling the reaction mixture it was quenched in a solution of sat. Sodiumbicarbonate and extracted several times with benzene. The reaction product was purified by Kugelrohr distillation followed by chromotography over silica gel. The product was obtained as a yellow oil.

EXAMPLE 40

The following Table I illustrates the antibacterial activity of compounds disclosed herein. The compounds were tested against several organisms set forth in Table I, according to the following procedure:

Compounds are prepared as a 6% solution in a suitable solvent such as water, ethanol or dimethylformamide. The 6% stock solution is then 5-fold serially diluted in test tubes to give the desired concentrations when mixed with agar and poured into sterile Petri dishes. Tryptone glucose extract agar is used as a medium for the bacterial testing. The plates are spot inoculated with a 24-hour nutrient broth culture of the bacteria to be tested and incubated at 37° C. for 48 hours. The plates are then examined visually for bacteria growth. The results, expressed in minimum inhibitory concentration

I claim:

1. A compound of the formula:

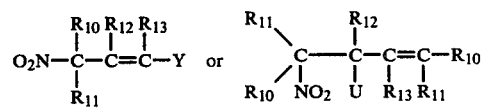

wherein $R_{10}$, $R_{11}$, $R_{12}$ and $R_{13}$ are lower alkyl or hydrogen, $$Y \text{ is } -CH_2O-\overset{O}{\underset{\|}{C}}-R_{26}, \quad U \text{ is } -O-\overset{O}{\underset{\|}{C}}-R_{26};$$

and $R_{26}$ is aryl which is unsubstituted or nuclear substituted by a halogen, lower alkoxy, carboxy, nitro, nitromethyl, amino or cyano.

2. The compound of claim 1 wherein said compound is

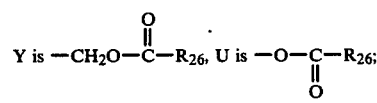

3. The compound of claim 1 wherein said compound is

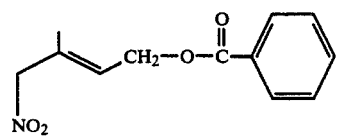

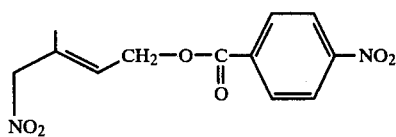
4. The compound of claim 1 wherein said compound is
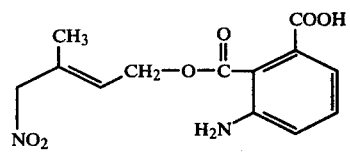
5. The compound of claim 1 wherein said compound is
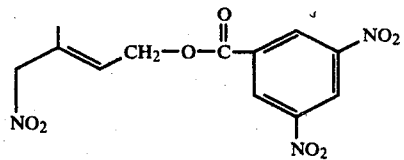
6. The compound of claim 1 wherein said compound is
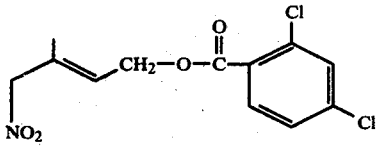
* * * * *